United States Patent
Svärd

(10) Patent No.: US 10,827,910 B2
(45) Date of Patent: Nov. 10, 2020

(54) BITE BLOCK FOR ENDOSCOPIC EXAMINATION WITH EXPANDING MEANS

(71) Applicant: Druiden Läkartjänst AB, Eksjö (SE)

(72) Inventor: Jan-Olof Svärd, Eksjö (SE)

(73) Assignee: DRUIDEN LAKARTJÄNST AB, Eksjö (SE)

( * ) Notice: Subject to any disclaimer, the term of this patent is extended or adjusted under 35 U.S.C. 154(b) by 144 days.

(21) Appl. No.: 16/094,012

(22) PCT Filed: Apr. 19, 2016

(86) PCT No.: PCT/EP2016/058655
§ 371 (c)(1),
(2) Date: Oct. 16, 2018

(87) PCT Pub. No.: WO2017/182058
PCT Pub. Date: Oct. 26, 2017

(65) Prior Publication Data
US 2019/0125171 A1    May 2, 2019

(51) Int. Cl.
*A61B 1/00* (2006.01)
*A61M 16/04* (2006.01)
*A61B 1/24* (2006.01)

(52) U.S. Cl.
CPC ...... *A61B 1/00154* (2013.01); *A61B 1/00147* (2013.01); *A61M 16/0488* (2013.01);
(Continued)

(58) Field of Classification Search
CPC .................. A61M 16/0488; A61M 16/0493
See application file for complete search history.

(56) References Cited

U.S. PATENT DOCUMENTS 2,820,457 A    1/1958 Phillips
2,936,625 A *  5/1960 Heiseler ............... F16B 7/20
                                                74/1 R
(Continued)

FOREIGN PATENT DOCUMENTS

EP    1407796 A1 *  4/2004    ........ A61M 16/0488
EP    1913968 A1    4/2008
(Continued)

OTHER PUBLICATIONS

International Search Report for International Application No. PCT/EP2016/058655, dated Jun. 10, 2016 (5 pages).

*Primary Examiner* — Kathryn E Ditmer
(74) *Attorney, Agent, or Firm* — Kagan Binder, PLLC

(57) ABSTRACT

A bite block (100) for use during endoscopic examination, comprising: —a bite block frame (101) sized and adapted to be fitted around a patient's mouth (401), —biting means (110) having a through hole (111) allowing a tube (301) to run through it, wherein the biting means protects the tube from the teeth of a patient (400) when in use, and —expanding means (122) connected to control means (200) for controlling the level of expansion of the expanding means, —wherein said expanding means are arranged onto holding means (120) being sized and adapted to be removably fitted into said trough hole of said biting means and wherein said holding means also comprise a through hole (121) allowing said tube to run through it. The bite block may be used without the holding means in the cases where no stopping function is needed.

4 Claims, 6 Drawing Sheets

(52) U.S. Cl.
CPC .... *A61M 16/0493* (2014.02); *A61M 16/0497* (2013.01); *A61B 1/24* (2013.01)

(56) References Cited

U.S. PATENT DOCUMENTS

| | | | | |
|---|---|---|---|---|
| 3,343,231 | A * | 9/1967 | Clay | F16G 11/048 24/136 R |
| 4,131,167 | A * | 12/1978 | Richey | E21B 17/1078 175/323 |
| 4,351,331 | A * | 9/1982 | Gereg | A61M 16/0488 128/207.17 |
| 4,906,234 | A * | 3/1990 | Voychehovski | A61M 16/0488 128/207.17 |
| 5,123,410 | A * | 6/1992 | Greene | A61M 16/0488 128/207.17 |
| 5,305,742 | A | 4/1994 | Styers et al. | |
| 5,413,095 | A * | 5/1995 | Weaver | A61M 16/0488 128/200.26 |
| 5,655,269 | A * | 8/1997 | Sagalovich | F16B 2/06 188/65.1 |
| 2002/0092526 | A1 * | 7/2002 | Bertoch | A61M 25/02 128/207.17 |
| 2002/0129816 | A1 | 9/2002 | Williams et al. | |
| 2002/0151871 | A1 * | 10/2002 | Gaiser | A61M 25/02 604/510 |
| 2006/0112962 | A1 * | 6/2006 | Tebbutt | A61M 16/0816 128/206.29 |
| 2007/0135770 | A1 * | 6/2007 | Hunt | A61B 1/00154 604/174 |
| 2007/0265497 | A1 * | 11/2007 | Brown | A61B 1/00149 600/114 |
| 2009/0255538 | A1 * | 10/2009 | Thomson | A61M 16/0493 128/207.17 |
| 2010/0217197 | A1 | 8/2010 | West et al. | |
| 2011/0108038 | A1 * | 5/2011 | Pierson | A61M 16/0497 128/207.14 |
| 2011/0180065 | A1 | 7/2011 | Hajgato et al. | |
| 2011/0284008 | A1 * | 11/2011 | Kanowitz | A61M 16/0497 128/207.17 |
| 2014/0246030 | A1 | 9/2014 | Puri et al. | |
| 2014/0261441 | A1 * | 9/2014 | Phillips | A61M 16/0497 128/207.14 |
| 2014/0261463 | A1 * | 9/2014 | Visconti | A61M 16/0497 128/861 |
| 2014/0332009 | A1 * | 11/2014 | Haider | A61M 16/0493 128/207.17 |

FOREIGN PATENT DOCUMENTS

| | | |
|---|---|---|
| GB | 2367009 A | 3/2002 |
| SE | 1400223 A1 | 11/2015 |
| WO | 0191838 A1 | 12/2001 |
| WO | 2007070457 A2 | 6/2007 |
| WO | 2014121199 A1 | 8/2014 |

* cited by examiner

BITE BLOCK FOR ENDOSCOPIC EXAMINATION WITH EXPANDING MEANS

CROSS-REFERENCE TO RELATED APPLICATIONS

This application claims priority to International Application No. PCT/EP2016/058655, filed Apr. 19, 2016 and titled "BITE BLOCK FOR ENDOSCOPIC EXAMINATION," the disclosure of which is incorporated herein by reference in its entirety.

TECHNICAL FIELD

The present invention relates to a bite block for endoscopic use.

BACKGROUND OF THE INVENTION

Endoscopic examinations are commonly used to examine the human body by inserting an endoscopic device through natural orifices of the patient. The examination and/or treatments may e.g. both visual examinations in real time, taking photographs, taking tissue samples, treatment of tumors or even removing unwanted objects such as bile-/gallstones or other surgical procedures.

Since the examination is uncomfortable for the patient, there is a risk that the patient bites the endoscopic tube in frustration or by reflexes. This is commonly prevented by inserting a biting block into the mouth before the examination starts which protects the endoscopic tube.

Controlling the endoscopic device is complicated and requires both experience and skill. Inability to control the endoscopic device in a desired way may lead to lengthy examination and even risk of serious complications for the patient.

In SE1400223 a state of the art bite block with inflatable expanding means is presented. The expanding means facilitates control of the device by allowing the operator to freeze the endoscopic device in a desired position by inflating the expandable means, e.g. for taking a sample or a photograph etc. However, the inventor has realized that there is room for improvements to this biting block.

SUMMARY OF THE INVENTION

The inventor has realized that the bite block may be further improved by separating the main body of the biting block from a holding means comprising the expandable means. Hereby, the bite block may be used without the holding means in the beginning of an examination, and only if needed in the specific case, the holding means may be inserted into the bite block, to facilitate the control of the endoscopic instrument. By separating the two parts of the biting block, a much cheaper product may be used in the cases where no stopping function is needed. Further, the examination time is reduced when compared to that two different bite blocks would to be used during the same examination, since the biting block may be used in two different states.

According to a first aspect of the invention above and other objectives are at least partly achieved by a bite block for use with e.g. endoscopic examination, comprising a bite block frame sized and adapted to be fitted around a patient's mouth, and biting means having a through hole allowing a tube to run through it. Further the biting means protects the tube from the teeth of a patient when the bite block is in use.

Moreover, the bite block comprises expanding means connected to control means for controlling the level of expansion of the expanding means. Further, the expanding means are arranged onto holding means being sized and adapted to be removably fitted into said through hole of said biting means and wherein said holding means also comprise a through hole allowing said tube to run through it.

Hereby, the bite block may be used without the holding means in the beginning of an examination, and only if needed in the specific case, the holding means may be inserted into the bite block, to facilitate the control of the endoscopic instrument.

By separating the two parts of the biting block (the holding means from the biting means) a much cheaper product may be used in the cases where no stop-function is needed. Further, the examination time is reduced when compared to that two different bite blocks would to be used during the same examination, since the biting block may be used in two different states, i.e. with or without the holding means.

In the context of this application endoscopic examination shall be interpreted as any type of examination, surgery, and/or any other use when inserting tubes into a patient, e.g. for gastric tubes or similar. This may include ultrasound examinations, biopsies, diagnostic samples or draining of e.g. cysts. Further, the tube may be a tube for any type of above-mentioned examination or surgery, such as an endoscopic tube.

In one embodiment, the biting means is a mouthpiece. The mouthpiece may have an outer surface sized and adapted to fit in the mouth of a patient. Further the outer surface may be constructed to withstand forces from a patient biting into it. Moreover, the mouthpiece may have a through hole for fitting the holding member.

In the context of this application the biting means may be an integrated portion of the bite block frame or be a separate part which is arranged onto the frame. Further, the holding means is a separate holding part, which is removable from the bite block frame. Further, in the same way, the expanding means may be an integrated portion of the holding means (part) or be a separate part which is arranged onto the holding means.

In one embodiment the holding means has an outer surface which is sized and adapted to mesh with the through hole of the biting means. The holding means may be formed as a channel or tube with the same outer form as the inner form of the through hole of the biting means.

In yet one embodiment the holding means comprise a longitudinal slit through its entire length, so as to allow an endoscopic tube to be inserted into the through hole of the holding means through the longitudinal slit.

Hereby, e.g. an endoscopic tube may remain in place inside of the patient and the holding means may be slipped onto the tube and then subsequently inserted into the through hole of the biting means. Hereby, the endoscopic tube does not have to be taken out before fitting the holding means into the biting means, which saves time and discomfort for the patient. Moreover, when e.g. an ultrasound examination is to be conducted, the tip of the tube comprises an ultrasound device, which often has a larger diameter than the tube itself. It may therefore be hard to fit the tip of the tube into the holding means' through hole. Thus, when the tube is equipped with an ultrasound device the slit as described above may enable the use of the holding means.

In the context of the application a slit should be considered as any type of dividing slit. The slit may be entirely closed so that the two facing edges of the holding means at slit are in contact, or even overlapped. Further, the slit may present an opening so that the two facing edged of the holding means at the slit are arranged at a distance from each other.

In yet one embodiment the opening width of said longitudinal slit is adjustable. Hereby, a slit with a small, or non-existing, opening width may be used. And the opening width may be increased once the holding means is to be slipped onto the tube.

In one embodiment the opening width of said longitudinal slit is adjustable by flexing the material of said holding means. Hereby, the holding means may in its material enable the variability in the opening width of the longitudinal slit. In other embodiments the holding means may comprise a component allowing an increase/decrease of the opening width of the slit, e.g. a hinge or the alike.

In one embodiment the holding means is produced in a flexible material such as e.g. a polymeric material, a synthetic or natural polymer, silicone, and/or rubber or similar. The material is preferably non-toxic and selected so that patients rarely are allergic to it.

In yet one embodiment the bite block comprises a gas connection means for connecting a gas supply directly to the bite block. Hereby, one less thing is required during the examination, namely a separate breathing mask. A separate breathing mask takes up space and may be inconvenient for the operator and the patient, so by including a gas connection means, the examination for both the operator(s) and the patient may be facilitated. In one embodiment, the gas connection means may be adapted to be coupled to an oxygen source or an anesthetic gas.

In yet one embodiment the bite block comprises attachment means for attaching said bite block to the head of a patient. Hereby, the bite block may be attached to the head of the patient, so as to avoid that it is moved out of position. A small movement of the bite block that also affects the endoscopic tube may result in a large movement inside the body. Thus by being able to strap the bite block to the head of the patient controlling the endoscopic tube may be facilitated.

In one embodiment the expanding means are expandable by means of fluid or mechanical expansion. In one embodiment, the expanding means comprise a flexible outer layer and an expandable cavity. The cavity may be filled with a fluid. In the context of this application, fluid should be interpreted as any type of gas or liquid. In one embodiment, the expanding means are expandable by means of fluid.

In yet one embodiment the control means is a lever. Hereby, controlling the expanding means may be easily operated by a person.

In yet one embodiment the control means is controllable by the foot or hand of an operator. Hereby, controlling the expanding means may be easily operated by a person during the examination or surgery. Further, if the control means is a foot lever, the user may utilize both his/her hands for other tasks, and control the expansion with his/her foot.

In yet one embodiment the holding means comprises coupling means adapted to be coupled to the biting means when said holding means is fitted into said through hole. Hereby, the holding means may be coupled to the biting means when it is fitted into the hole of the biting means, so that the biting means is not accidently unfitted from said hole of the biting means. In one embodiment the coupling means is a mechanical coupling.

In yet one embodiment the biting means comprises coupling means corresponding to the coupling means of said holding means.

In one embodiment, the holding means comprise two coupling means, which each is adapted to be coupled to the biting means when said holding means is fitted into said through hole of the biting means. In yet one embodiment, the biting means also has two coupling means corresponding to coupling means of said holding means. The coupling means may be a male member cooperating with a female member, wherein one of the male and female members is a part of the coupling means of the holding means, and the other one is a part of the biting means. In one embodiment, the coupling means may be a flexible hatch element having a protruding portion being sized and formed to engage an aperture. The protruding portion and the aperture may be a part of either the holding means or the biting means.

In one embodiment the control means comprises a locking function for locking the expandable means in an expanded state. The locking function may be mechanical, electrical or other type of locking function. Hereby, the operator does not have to hold the control means in a locked position, but once the expanding means are expanded the operator may release the control means and concentrate on other tasks, such as taking a photo or a sample, changing instruments, inserting devices etc.

In one embodiment the expanding means is a helical spring. In further one embodiment the helical spring is sized and adapted to be fitted onto said tube 301. In yet one embodiment the helical spring is further configured to be expandable in longitudinal length by means of said control means, so that the cross-sectional diameter of said helical spring is decreased and the tube is held in a fixed position relative the bite block by means of said helical spring.

Hereby, the expanding means may be achieved by an off the shelf helical spring and thereby springs sized and adapted for different tube sizes will be easily found. Further, the holding force from the expanding means is spread throughout the length of the helical spring and so as to avoid damages to the tube.

According to another aspect of the invention there is provided a method for using a bite block, comprising the steps of: providing a bite block comprising a bite block frame sized and adapted to be fitted around a patient's mouth and biting means having a through hole. Thereafter, a step of providing a tube of a medical instrument, such as an endoscopic instrument, into said through hole of said biting means. The method further comprises the step of fitting a holding means into the through hole of said biting means, wherein said holding means comprise expanding means connected to control means for controlling the level of expansion of the expanding means, so that said endoscopic tube runs through the through hole of the holding means.

The advantages of this method are largely analogous to the advantages of the first aspect of the inventive concept, namely that the bite block may be used without the holding means in the beginning of an examination, and only if needed in the specific case, the holding means may be inserted into the bite block, to facilitate the control of the endoscopic instrument. By separating the two parts of the biting block, a much cheaper product may be used in the cases where no stopping function is needed and examination time may be reduced.

In one embodiment the holding means comprises a longitudinal slit through its entire length, and before the step of fitting the holding means into the through hole of the biting means a step of fitting the holding means onto the endoscopic tube via the longitudinal slit is performed.

As discussed above, having a longitudinal slit in the holding means enables having the endoscopic tube remained in place in the patient while slipping the holding means onto the tube and subsequently inserting it into the through hole of the biting means. Hereby, time may be saved and the patient may be less affected than compared to if the tube were to be taken out and the put back into the patient.

In one embodiment the step of fitting the holding means onto the endoscopic tube via the longitudinal slit is performed by increasing the width of the longitudinal slit when fitting the holding means onto the endoscopic tube. Hereby, the slit may be smaller than the diameter of the endoscopic tube and only opened temporarily as the tube is inserted into the through hole of the holding means.

In yet one embodiment the method further comprise the step of connecting a gas supply for a patient onto a gas connection means. Hereby, no separate gas supply mask is needed during the examination or surgery.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

Figure 1:
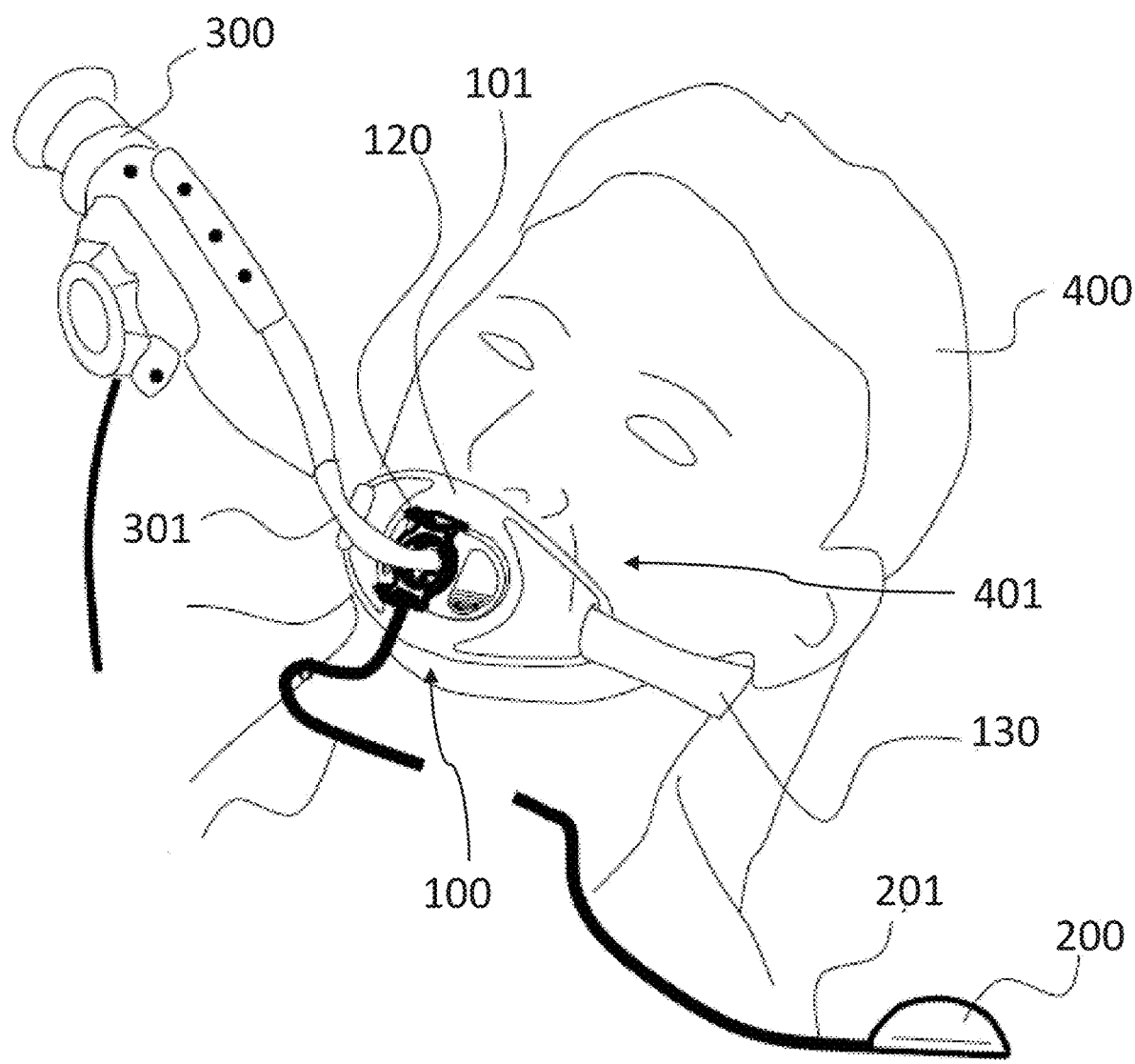
FIG. 1 is an illustration of a patient going through an endoscopic examination with a bite block.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout the application. Further, some elements appear several times in a drawing, and for clarity reasons not all of these elements have been appointed a reference in the drawings.

In the following, the bite block is described to be used in connection with endoscopic examinations and/or surgeries. It should however also be understood that the biting block may be used for other applications when a tube is to be inserted into a patient, e.g. for gastric tubes or similar. Examples of such procedures are, as also mentioned above, any type of examination, surgery, and/or any other use when inserting tubes into a patient, e.g. for gastric tubes or similar. This may include ultrasound examinations, biopsies, diagnostic samples or draining of e.g. cysts.

FIG. 1 is an illustration of a patient 400 going through an endoscopic examination with a bite block 100 in the patient's mouth 401. The examination is carried out with an endoscopic device 300 having an endoscopic tube 301 connected to the device 300 and running through the bite block and into the patient. Further, the bite block is strapped around the patient's head by attachment means, so that the bite block is not removed from the mouth by accident. Further, the bite block 100 comprise a frame 101 and holding means 120 which will be described more in detail below. The holding means, which comprise the expanding means (not shown in FIG. 1) is connected to a control means 200 adapted to control the level of expansion of the expanding means. The control means 200 may be a lever that can be operated by e.g. a hand or a foot of a user. In the illustrated embodiment the control means 200 may be compressed to move a fluid towards the expanding means to cause them to expand and thereby locking the endoscopic tube 301 in place.

Figure 2:
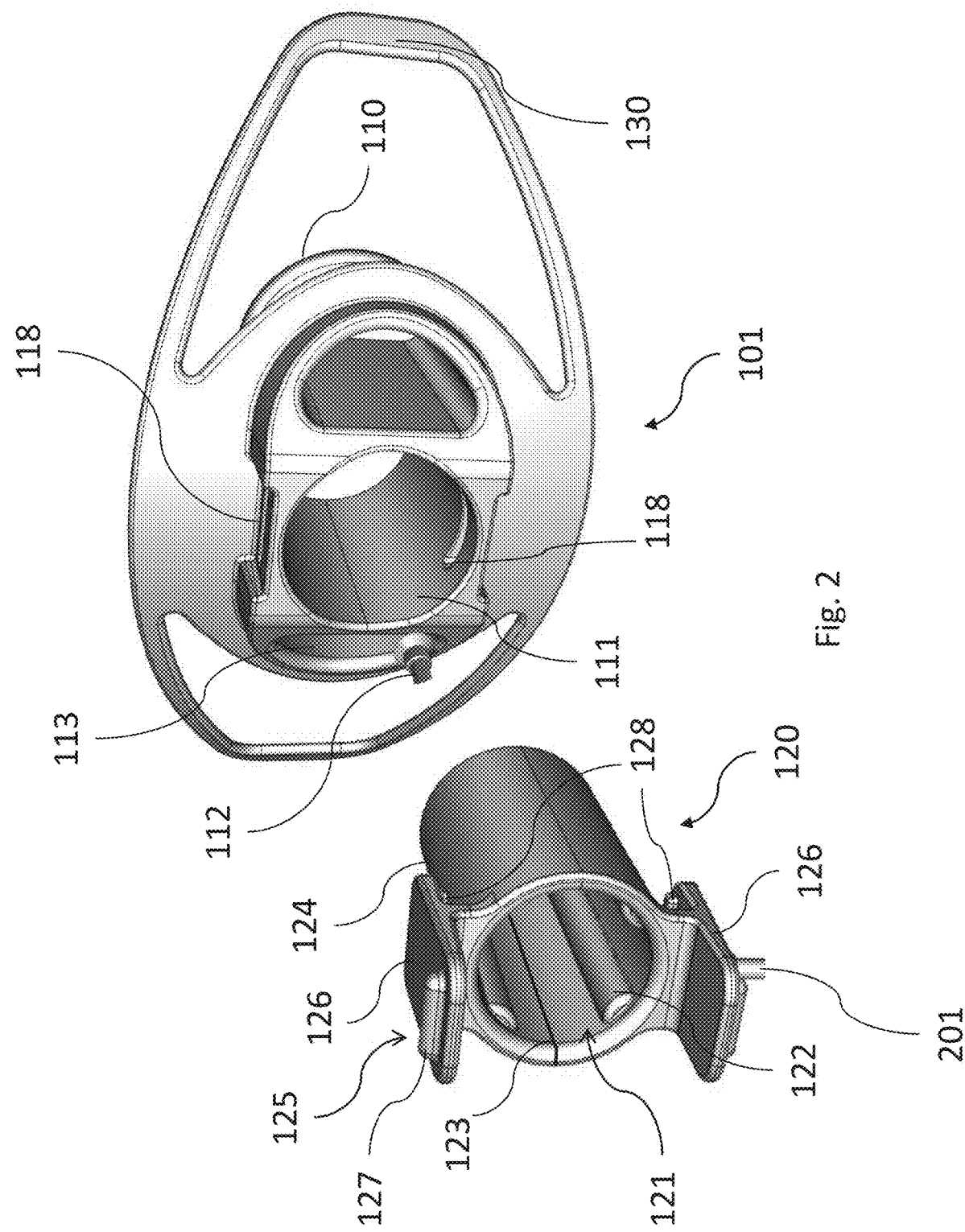
FIG. 2 is a perspective view of holding means and bite block frame.

FIG. 2 is a perspective view of the holding means 120 and the bite block frame 101. The holding means 120 in the illustrated embodiment comprises four expanding means 122. It is of course possible to have another number of expanding means, such as two, three five or more. It could also be possible to have a single expansion means. The expanding means in the illustrated embodiment are longitudinal portions which expand upon an increased pressure generated in the control means 200. When the expanding means expand they restrict the free area in the through hole 121 of the holding means 120 and thereby prevent the endoscopic tube 301 to move relative the holding means 120.

The holding means is sized and formed to mesh with the through hole of the through hole 111 of the biting means 110 in the frame 101. The outer surface 124 of the cylindrical body of the holding means is dimensioned to mesh with the inner surface of the through hole 111 of the biting means 110.

Further, the holding means 120 comprise coupling means 125 for coupling the holding means to the biting means. The coupling means may be formed in a number of ways, but in the illustrated embodiment the coupling means comprise a pivotable body 126. The pivotable body 126 is connected to the cylindrical body of the holding means at a middle portion. Further at an outer end, there is a gripping protrusion 127 to facilitate gripping of the pivotable body. In the opposite end there is an engaging protrusion 128 which is sized and formed to engage with a corresponding aperture 118 in the biting block frame. In the illustrated embodiment there are two coupling means at two opposing sides of the biting means. In other embodiments there may be any number of coupling means. The pivotable body 126 makes it possible to press the outer portion towards the center of the holding means, and thereby lift the inner portion having the engaging protrusion 128 so as to allow it to freely be inserted into the through hole 111 of the biting means. Thereafter, the pivotable body may be released so that the engaging protrusion engages the corresponding aperture 118 in the biting block frame. The pivotable movement may be enabled by a flexible material. Either the whole body of the holding means and/or the body of the coupling means may be of a flexible material, or only selected parts of the pieces may be flexible.

The holding means 120 is further coupled to the control means by a connecting means 201 being a connecting tube for transporting fluid between the control means 200 and the expanding means 122. In other embodiments, where mechanical expansion means are used, the connection may be e.g. a wire transporting mechanical movement or an electrical cable for transmitting a control signal.

The holding means 120 in the illustrated embodiment further comprise a slit 123. The slit 123 runs throughout the length of the holding means. The slit in the illustrated example is closed in its original position, but may be opened by pushing (or pulling) the two portions of either side of the slits from each other. When the halves are parted the slits is opened. When opened enough, an endoscopic tube may be inserted in a direction being radial relative cylindrical body of the holding means.

FIG. 2 further illustrates the frame part 101 of the biting block. The bite block frame comprises the biting means 110 (which is more clearly illustrated in FIG. 4 and described below). The frame comprises a gas connection means 112 for allowing a user to connect a gas supply to the bite block. The gas connection means may be a pipe nipple for connecting a gas tube onto. It may also be any type of fast-coupling, screw-coupling or other for connecting a gas supply to the gas connection means 112.

As briefly discussed above, the frame has an aperture 118 for receiving the engaging part 128 of the coupling means 125 of the holding means. There may be two apertures or more apertures 118 in the frame. There may be one for each protruding portion 128 of the holding means or even two for each protruding portion 128 of the holding means so as to facilitate coupling of the two pieces to each other.

Moreover, the frame 101 may comprise breathing vent holes 113 for allowing airflow between the mouth of a patient and the exterior of the bite block during use. In the illustrated embodiment there are two air vent holes 113, one on each side, but there may be any number of vent holes as long at air is permitted to flow through the biting means of the bite block.

Further, the frame comprises attachment means 130 at the outer ends of the frame. In the illustrated embodiment, there is one attachment point at each side of the frame. E.g. the attachment means 130 may be coupling points for attaching an elastic band around the head of the patient 400.

Figure 3:
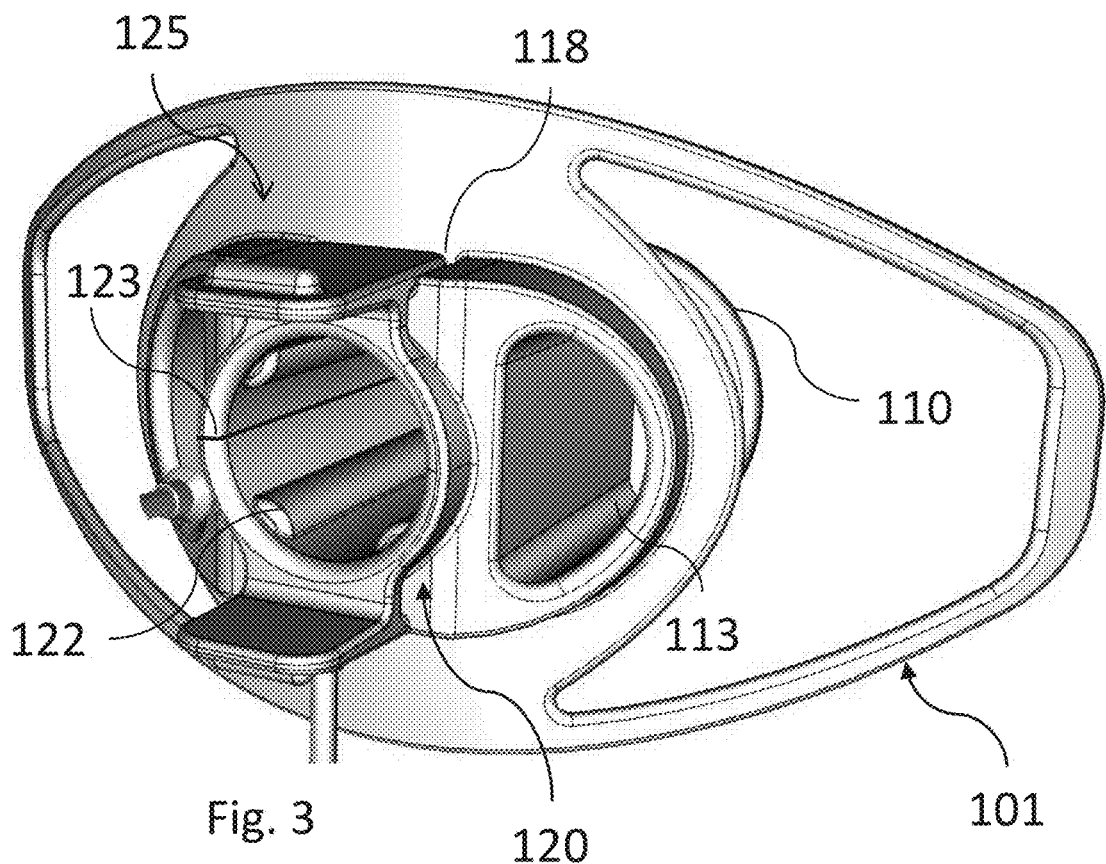
FIG. 3 is a perspective front view of a bite block.

FIG. 3 is a perspective front view of the bite block 100 where the holding means 120 is inserted into the through hole of the biting means 110. The coupling means 125 are in mechanical positive connection with the frame 101. This is achieved by that the two engaging protrusions are inserted into two corresponding apertures 118 in the frame.

Figure 4:
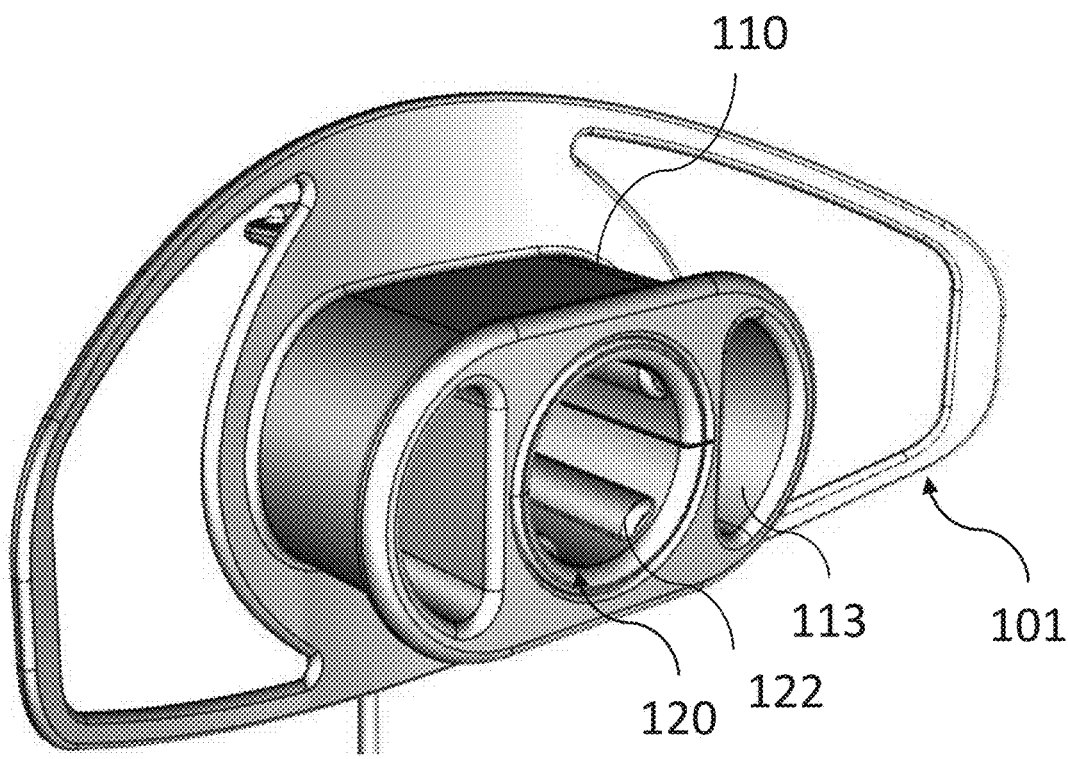
FIG. 4 is a perspective backside view of a bite block.

FIG. 4 illustrates the same bite block but is a perspective backside view of the bite block. From this side, the biting means 110 is more clearly illustrated. The biting block may have an elliptical shape to correspond to a patient's lips. Hereby, a patient may put the lips around the biting means and rest the teeth on the biting means 110. The patient may further breathe through the air vent holes 113 inside the biting means 110. The slit 123 is also illustrated from the backside, as it runs along the entire longitudinal length of the biting means. Moreover, the expanding means are shown inside the through hole of the holding means 120.

Figure 5:
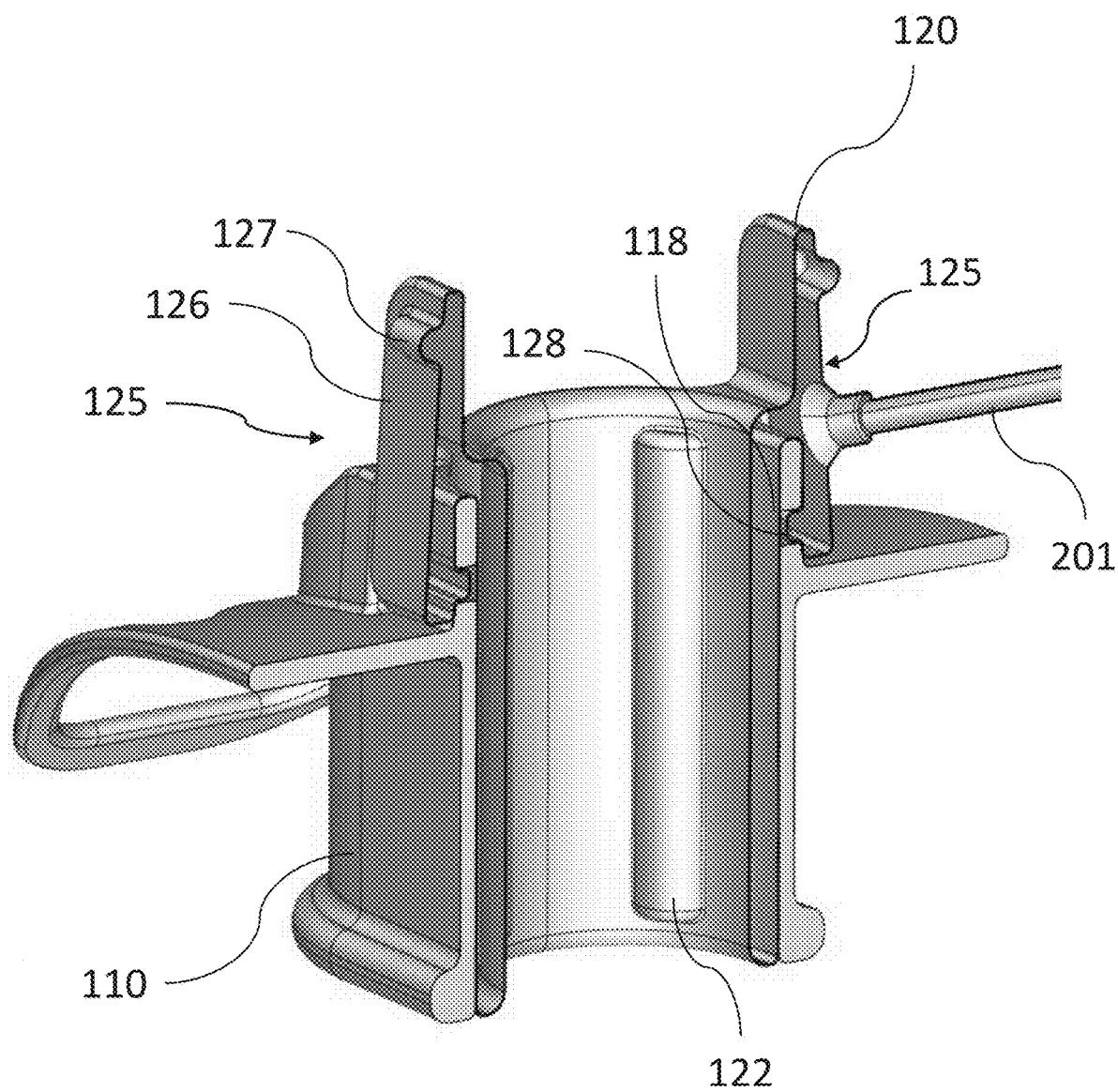
FIG. 5 is a cross-sectional view of a bite block.

FIG. 5 is a cross-sectional view of a bite block, and illustrates how the holding means 120 is held in the through hole 111 of the biting means 110 by the coupling means 125 arranged on two opposite sides of the through hole. The engaging protrusion 128 is inserted into the aperture 118 so as to lock the holding means 125 in the through hole of the biting means 110. Hereby, the holding means is prevented from accidently move axially relative the biting means 110. Further the expansion means 122 are clearly illustrated in the through hole of the holding means. Moreover, the connecting tube 201 running to the control means 200 is illustrated in the figure, and how it is connected to the holding device for delivering expansion fluid to the expansion means 122. The expansion fluid may e.g. be a saline solution (NaCl in water) or sterile $H_2O$ or any other non-toxic fluid including gas. The slit 123 is not shown in FIG. 5 but may be in the half of the biting block 100 which is not displayed in the cross-section of FIG. 5.

Figure 6:
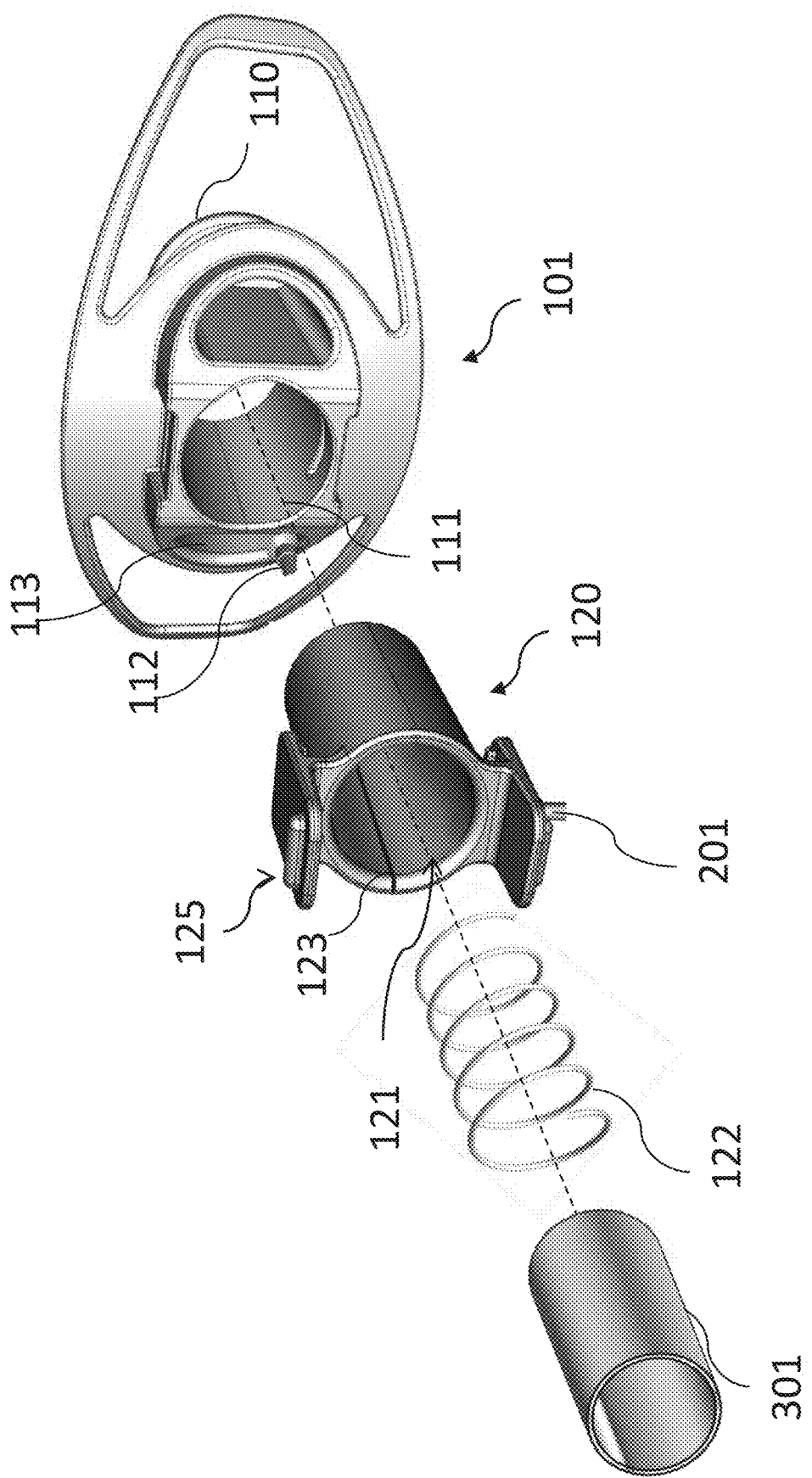
FIG. 6 is an exploded perspective front view of a bite block.

FIG. 6 is an exploded perspective front view of a bite block wherein the expanding means 122 is a helical spring. In this embodiment, the helical spring is initially slipped onto the tube 301 (only a section of the tube is displayed in FIG. 6) and through the through holes 111, 121 of the holding means 120 and the biting means 110. Further, the helical spring, acting as the expanding means 122, is in one end portion connected to the bite block so that it is prevented from moving that portion relative the bite block when another end portion is pushed or pulled by means of the connecting means 201. The connecting means is preferably a mechanical connection such as a wire, shaft or other mechanical means for transferring a control movement from the control device 200 to the expansion means 122 being the helical spring. When the helical spring is expanded in length compared to its basic position the cross-sectional diameter of the spring decrease. Consequently, the tube running through the helical spring (acting as expansion means) may be held still relative the bite block by extending the length of the spring enough. A clear advantage with using a spring is that the force holding the tube still is spread over the entire length of the expansion means (helical spring). Further, since helical springs exist in many sized and dimensions the helical spring may be chosen to fit the tube which is to be used during the procedure/examination.

Figure 7:
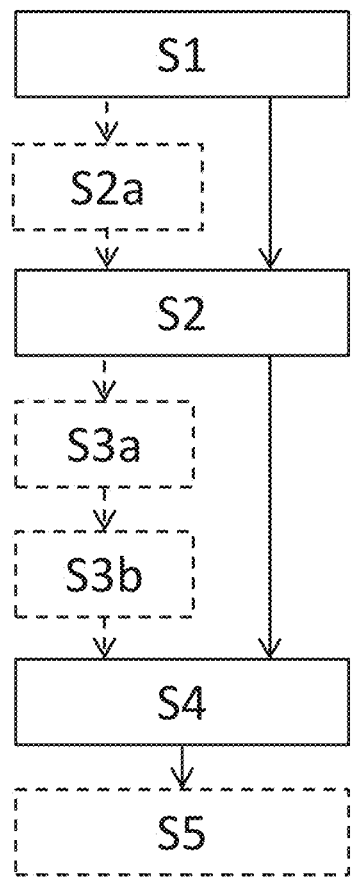
FIG. 7 is a schematic block diagram of a method of using a bite block.

FIG. 7 is a schematic block diagram of a method of using a bite block. The method comprise the steps of S1 providing a bite block comprising a bite block frame 101 which is sized and adapted to be fitted around a patient's mouth 401, i.e. according to any of the embodiments as described above. Thereafter the step S2 of providing a tube 301 of e.g. the endoscopic instrument into the through hole 111 of the biting means 110. In the case where a helical spring is used for expansion means 122 (as shown in FIG. 6 and described above), an optional step 2a where the helical spring is slipped onto the tube 301 before the tube is inserted into the through holes 111, 121 may be performed. As an alternative to the step 2a, the helical spring may be slipped onto the tube 301 when the holding means 120 is slipped onto the tube as described below in step After the second step, an optional step S3a may be performed by opening the holding means 120 along the longitudinal slit 123, so that the width of the longitudinal slit 123 is increased. Thereafter another optional step S3b is performed which is fitting the holding means 120 onto the endoscopic tube 301 via the longitudinal slit 123. The holding means is then slipped onto the endoscopic tube at a position between the endoscopic instrument 300 and the biting means 110.

After these steps, the fourth step of fitting S4 the holding means 120 into the through hole 111 of the biting means 110 is conducted. The holding means comprise the expanding means 122 (regardless of what type of expanding means) connected to control means 200 by the connecting means 201 for controlling the level of expansion of the expanding means as is described above. Hereby, the endoscopic tube 301 runs through the through hole of the holding means 120.

Finally, an optional step S5 of connecting a gas supply for a patient onto the gas connection means 112 may be performed.

The invention claimed is:

1. A method for using a bite block, comprising the steps:
providing a bite block comprising a bite block frame sized and adapted to be fitted around a patient's mouth and biting means having a through hole, wherein said biting means comprises a holding means having a longitudinal slit through its entire length,
providing a tube of a medical instrument into said through hole of said biting means,
further comprising the steps of
fitting the holding means onto the tube via the longitudinal slit,
and then fitting the holding means and the tube into the through hole of said biting means, wherein said holding means comprise expanding means connected to control means for controlling the level of expansion of the expanding means, so that said tube runs through a through hole of the holding means.

2. The method according to claim 1, wherein said expanding means is a helical spring and said helical spring is slipped onto the tube before said tube is fitted into the through hole of said biting means.

3. The method according to claim 1, wherein the step of fitting the holding means onto the tube via the longitudinal slit is performed by increasing the width of the longitudinal slit when fitting the holding means onto the tube.

4. The method according to claim 1, further comprising the step of connecting a gas supply for the patient onto a gas connection means of the bite block.

\* \* \* \* \*